(12) United States Patent
Song et al.

(10) Patent No.: US 11,684,325 B2
(45) Date of Patent: Jun. 27, 2023

(54) PATIENT SITTING EQUIPMENT FOR RADIOTHERAPY

(71) Applicant: HEFEI CAS ION MEDICAL AND TECHNICAL DEVICES CO., LTD., Hefei (CN)

(72) Inventors: Yuntao Song, Hefei (CN); Jianghua Wei, Hefei (CN); Yonghua Chen, Hefei (CN); Kaizhong Ding, Hefei (CN); Sumei Liu, Hefei (CN); Changjian Luo, Hefei (CN); Xiaoyang Pan, Hefei (CN)

(73) Assignee: HEFEI CAS ION MEDICAL AND TECHNICAL DEVICES CO., LTD., Hefei (CN)

( * ) Notice: Subject to any disclaimer, the term of this patent is extended or adjusted under 35 U.S.C. 154(b) by 0 days.

(21) Appl. No.: 17/972,746

(22) Filed: Oct. 25, 2022

(65) Prior Publication Data

US 2023/0043606 A1 Feb. 9, 2023

Related U.S. Application Data

(63) Continuation of application No. PCT/CN2021/126380, filed on Oct. 26, 2021.

(30) Foreign Application Priority Data

Sep. 26, 2021 (CN) .......................... 202111129254.X (51) Int. Cl.
A61B 6/04 (2006.01)
(52) U.S. Cl.
CPC ................................. *A61B 6/0487* (2020.08)

(58) Field of Classification Search
CPC .......... A61B 6/00; A61B 8/04; A61B 6/0487; A61B 6/04
See application file for complete search history.

(56) References Cited

U.S. PATENT DOCUMENTS

| 2004/0098804 | A1* | 5/2004 | Varadharajulu | A61B 6/0487 5/607 |
| 2008/0292053 | A1* | 11/2008 | Marash | A61B 6/04 378/65 |
| 2014/0139215 | A1* | 5/2014 | Gregerson | A61B 6/027 324/309 |

FOREIGN PATENT DOCUMENTS

| CN | 203914943 U | 11/2014 |
| CN | 105079986 A | 11/2015 |
| CN | 107007946 A | 8/2017 |
| CN | 109793997 A | 5/2019 |
| CN | 211097098 U | 7/2020 |

(Continued)

*Primary Examiner* — Fredrick C Conley (57) ABSTRACT

Patient sitting equipment for radiotherapy, including an installation platform, a treatment couch assembly, a support and adjustment assembly and a 3D imaging assembly. The treatment couch assembly is configured to fix a patient. The support and adjustment assembly is configured to adjust a position of the treatment couch assembly with respect to the installation platform. The 3D imaging assembly includes a column assembly and a 3D imaging device. The column assembly is arranged at the installation platform, and extends along the vertical direction. The 3D imaging device is movably arranged at the column assembly, and is corresponding to the treatment couch assembly in a horizontal projection direction. The 3D imaging device is configured to scan the patient.

5 Claims, 5 Drawing Sheets (56) References Cited

FOREIGN PATENT DOCUMENTS

| CN | 113288702 A | 8/2021 |
|----|-------------|--------|
| JP | H09122118 A | 5/1997 |

* cited by examiner

PATIENT SITTING EQUIPMENT FOR RADIOTHERAPY

CROSS-REFERENCE TO RELATED APPLICATIONS

This application is a continuation of International Patent Application No. PCT/CN2021/126380, filed on Oct. 26, 2021, which claims the benefit of priority from Chinese Patent Application No. 202111129254.X, filed on Sep. 26, 2021. The content of the aforementioned application, including any intervening amendments thereto, is incorporated herein by reference in its entirety.

TECHNICAL FIELD

The disclosure relates to radiotherapy, and more specifically to patient sitting equipment for radiotherapy.

BACKGROUND

As predicted by the Cancer Research UK, there will be about 24 million new cases of cancer each year by 2030. Proton therapy is currently one of the most advanced radiation therapy techniques, which uses a high-energy proton beam instead of X-ray to treat cancer.

Compared with the traditional radiation, protons can better target the tumor area through the "Bragg peak" effect, and the normal tissues in the posterior area of the tumor will be hardly exposed to radiation, leading to a higher survival rate.

The treatment is performed mainly in a rotary treatment room or a fixed treatment room. When it is required to treat multiple parts of a patient, a large rotating frame is generally employed to assist the scanning of the patient, which leads to high cost and large space occupation. The fixed treatment room can only be applied to limited types of tumors.

SUMMARY

An object of the present disclosure is to provide patient sitting equipment for radiotherapy, which has an image scanning function, and has reduced cost and improved treatment efficiency.

Technical solutions of this application are specifically described as follows.

This application provides patient sitting equipment for radiotherapy, comprising:
an installation platform;
a treatment couch assembly;
a support and adjustment assembly; and
a three-dimensional (3D) imaging assembly;
wherein the treatment couch assembly is configured to fix a patient;
the support and adjustment assembly is arranged below the installation platform; and the support and adjustment assembly is connected to the treatment couch assembly, and is configured to adjust a position of the treatment couch assembly with respect to the installation platform; and
the 3D imaging assembly comprises a column assembly and a 3D imaging device; the column assembly is arranged at the installation platform, and extends along the vertical direction; the 3D imaging device is movably arranged at the column assembly; the 3D imaging device is corresponding to the treatment couch assembly in a horizontal projection direction; and the 3D imaging device is configured to perform image scanning on the patient.

Regarding the patient sitting equipment provided herein, the patient's posture can be fixed by means of the treatment couch assembly. The position of the treatment couch assembly can be adjusted through the support and adjustment assembly, so as to adjust the patient's position. Therefore, the sitting equipment can facilitate the scanning and radiation therapy for multiple parts of the patient or the multi-angle scanning and radiation therapy for the same part. By means of the sitting equipment provided herein, the multi-direction and multi-angle treatment and scanning can be achieved, reducing the operation cost and space occupation.

In some embodiments, the treatment couch assembly comprises a base, a treatment couch main body and a lifting-lowering assembly;
the base is connected to the support and adjustment assembly;
the treatment couch main body is arranged on the base, and is configured to fix the patient; and
the lifting-lowering assembly is arranged above the base, and is connected to the treatment couch main body to drive the treatment couch main body to move up or down.

In some embodiments, the treatment couch main body comprises a mounting base, a couch plate and a cushion;
the mounting base is connected to the lifting-lowering assembly;
the couch plate is arranged on the mounting base, and extends upwards along the vertical direction; and the couch plate is configured to deflect in a first direction with respect to the mounting base to adjust depression and elevation angles of the couch plate; and
the cushion is arranged on the mounting base, and at a bottom end of the couch plate; and the cushion is configured to be turned over.

In some embodiments, the treatment couch assembly further comprises a leg limit block and feet limit block;
the leg limit block is arranged on the base, and extends along the vertical direction from an upper surface of the base; and the leg limit block is configured to limit legs of the patient; and
the foot limit block is arranged at the upper surface of the base, and is located between the leg limit block and the lifting-lowering assembly; and the foot limit block is configured to limit feet of the patient.

In some embodiments, the support and adjustment assembly comprises a treatment couch adjustment assembly; and the treatment couch adjustment assembly is connected to a base of the treatment couch assembly;
the treatment couch adjustment assembly comprises a horizontal moving platform, a rotating platform and a tilting platform;
the horizontal moving platform is configured to adjust a position of the base with respect to the installation platform in the horizontal direction;
the rotating platform is connected to the horizontal moving platform; and the rotating platform is configured to drive the base to rotate horizontally with respect to the installation platform;
the tilting platform is connected between the rotating platform and the base; the tilting platform is configured to drive the base to tilt with respect to the installation platform; and the horizontal moving platform, the rotating platform and the tilting platform are sequentially arranged from bottom to top.

In some embodiments, the tilting platform comprises a tilting platform main body, a connecting rod assembly and a drive motor;

the tilting platform main body is arranged above the rotating platform;

the connecting rod assembly is connected between the tilting platform main body and the base;

the drive motor is connected to the connecting rod assembly; and the drive motor is configured to drive the connecting rod assembly to move to tilt the base with respect to the tilting platform main body.

In some embodiments, the support and adjustment assembly further comprises a support assembly; the support assembly is arranged at a bottom of the installation platform; the treatment couch adjustment assembly is arranged on the support assembly; and the support assembly is configured to drive the treatment couch adjustment assembly to move up or down with respect to the installation platform.

In some embodiments, the column assembly comprises a fixed column, a rotating column and a rotating assembly;

the fixed column is arranged on the installation platform, and extends along the vertical direction;

the 3D imaging device is connected to the rotating column; the rotating column is arranged at a side of the fixed column close to the treatment couch assembly; and the rotating column is rotatably connected to the fixed column; and the rotating assembly is connected to the fixed column and the rotating column; and the rotating assembly is configured to drive the rotating column to rotate with respect to the fixed column.

In some embodiments, the rotating column is provided with a sliding groove; the sliding groove extends along a length direction of the rotating column; and the column assembly further comprises a drive member; the drive member is connected to the rotating column and the 3D imaging device; and the drive member is configured to drive the 3D imaging device to slide with respect to the rotating column.

In some embodiments, the number of the column assembly is two; two column assemblies are respectively arranged at two sides of the treatment couch assembly; and the 3D imaging device is respectively connected to two rotating columns of the two column assemblies.

The additional aspects and advantages of the present disclosure will become apparent below with reference to the description or embodiments.

BRIEF DESCRIPTION OF THE DRAWINGS

The aspects and advantages of the present disclosure will become apparent and easily understood below with reference to the embodiments and accompanying drawings.

In the drawings:
100, patient sitting equipment;
10, installation platform;
20, treatment couch assembly;
21, first base;
22, treatment couch main body;
221, mounting base;
222, couch plate;
2221, frame;
223, cushion; 224, armrest;
23, lifting-lowering assembly;
24, leg limit block;
25, foot limit block;
30, support and adjustment assembly;
31, treatment couch adjustment assembly;
311, horizontal moving platform;
312, rotating platform;
313, tilting platform;
3131, tilting platform main body;
3132, connecting rod assembly;
32, support assembly;
321, actuation cylinder;
322, telescopic rod;
33, second base;
40, 3D imaging assembly;
41, column assembly;
411, fixed column;
412, rotating column;
4121, sliding groove;
413, rotating assembly;
4131, drive device;
4132, slewing bearing;
414, drive member; and
42, 3D imaging device.

DETAILED DESCRIPTION OF EMBODIMENTS

It should be noted that the same or similar reference numerals in the accompanying drawings indicate the same or similar elements or elements with the same or similar function. Described below are merely illustrative of the disclosure, and are not intended to limit the disclosure.

Patient sitting equipment 100 of the present disclosure will be described below with reference to FIGS. 1-5.

Figure 1:
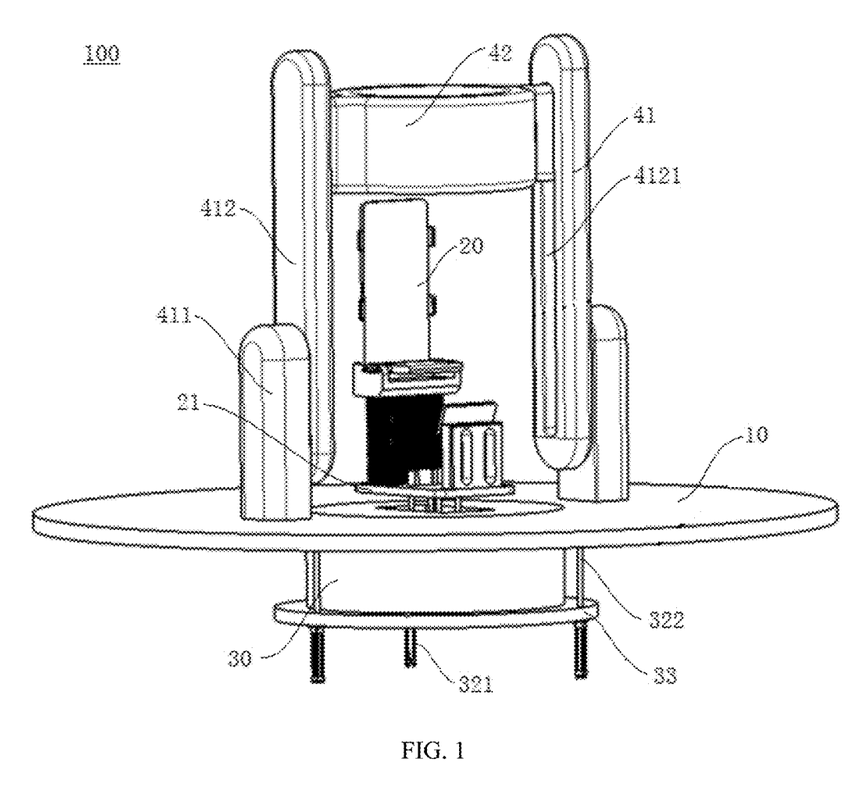
FIG. 1 schematically shows a structure of patient sitting equipment for radiotherapy according to an embodiment of the disclosure.

Referring to FIG. 1, the patient sitting equipment 100 includes an installation platform 10, a treatment couch assembly 20, a support and adjustment assembly 30 and a 3D imaging assembly 40. The patient sitting equipment 100 has an image scanning function, which will be exemplarily described below.

The installation platform 10 is configured as installation carrier for the treatment couch assembly 20, the support and adjustment assembly 30 and the 3D imaging assembly 40. The installation platform 10 is ground, or a frame structure embedded in the ground.

Referring to FIG. 1, the treatment couch assembly 20 is configured to fix a patient to facilitate the image scanning by the 3D imaging assembly 40. The support and adjustment assembly 30 is arranged below the installation platform 10, and is connected to the treatment couch assembly 20. The support and adjustment assembly 30 is configured to adjust a position of the treatment couch assembly 20 with respect to the installation platform 10, so as to allow the patient at an appropriate scanning angle and position to allow a good scanning effect. The installation platform 10 is provided with a through hole. The support and adjustment assembly 30 is connected to the treatment couch assembly 20 through the through hole, and is configured to support the treatment couch assembly 20 and adjust the position of the treatment couch assembly 20. It should be understood that the through hole facilitates the connection between the support and adjustment assembly 30 and the treatment couch assembly 20, thereby reducing the space occupation.

In an embodiment, the 3D imaging assembly includes a column assembly 41 and a 3D imaging device 42. The column assembly 41 is arranged on the installation platform 10, and extends along the vertical direction. The 3D imaging device 42 is movably arranged at the column assembly 41. The 3D imaging device 42 is corresponding to the treatment couch assembly 20 in a horizontal projection direction. The 3D imaging device 42 is configured to perform image scanning on the patient.

Specifically, the column assembly 41 is configured to support and fix the 3D imaging device. A position of the 3D imaging device 42 with respect to the column assembly 41 can be adjusted according to a scanning requirement, such that a position of the 3D imaging device 42 with respect to the treatment couch assembly 20 (also the patient) can be adjusted. Therefore, the 3D imaging device 42 can be adjusted to an appropriate position for image scanning of multiple parts, further ensuring the scanning effect of the patient sitting equipment 100.

The treatment couch assembly 20 fixes the patient, such that the patient can keep a posture suited for image scanning. The support and adjustment assembly 30 adjusts the position of the treatment couch assembly 20 with respect to the installation platform 10, such that a to-be-scanned part of the patient is located at an area corresponding to the 3D imaging device 42. The 3D imaging device 42 is further adjusted to be located at a scanning position facilitating to scan the to-be-scanned part of the patient, which ensures the scanning effect of the patient sitting equipment 100. The patient sitting equipment fixes the patient's posture firstly, and then the 3D imaging device 42 is adjusted to be corresponded to the patient through a multi-stage adjustment, consequently, the scanning effect of the patient sitting equipment 100 can be improved.

It should be understood that the position of the patient can be adjusted through the support and adjustment assembly 30 if a multi-angle image scanning is required, and the position of the 3D imaging device 42 can be then adjusted. Therefore, the patient sitting equipment 100 can satisfy scanning and treatment for multiple parts or multi-angle of the same part. The patient is required no various postures and the patient sitting equipment 100 is free from repeated activation, thereby reducing production cost, operation and maintenance of the patient sitting equipment 100.

It should be noted that the treatment for cancer patients is usually performed in a rotary treatment room or a fixed treatment room. When multiple parts of patient need to be treat, a large rotating frame is generally employed which leads to large space occupation. The fixed treatment room can only be applied to limited types of tumors. In addition, the equipment and supporting buildings of these treatment rooms (the rotary treatment room or the fixed treatment room) are expensive. Regarding the patient sitting equipment 100, the position of the treatment couch assembly 20 and that of the 3D imaging device 42 are adjusted to allow the patient to be corresponded to the 3D imaging device 42. The patient sitting equipment 100 is easy to be adjusted, and has smaller space occupation with respect to the normal rotary treatment room or fixed treatment room, which reduces the cost.

Regarding the patient sitting equipment 100, the patient's posture can be fixed by means of the treatment couch assembly 20. The position of the treatment couch assembly 20 can be adjusted through the support and adjustment assembly 30, so as to adjust the patient's position. Therefore, the patient sitting equipment 100 can facilitate the scanning and radiation therapy for multiple parts of the patient or the multi-angle scanning and radiation therapy for the same part. By means of the patient sitting equipment 100, the multi-direction and multi-angle treatment and scanning can be achieved.

Figure 4:
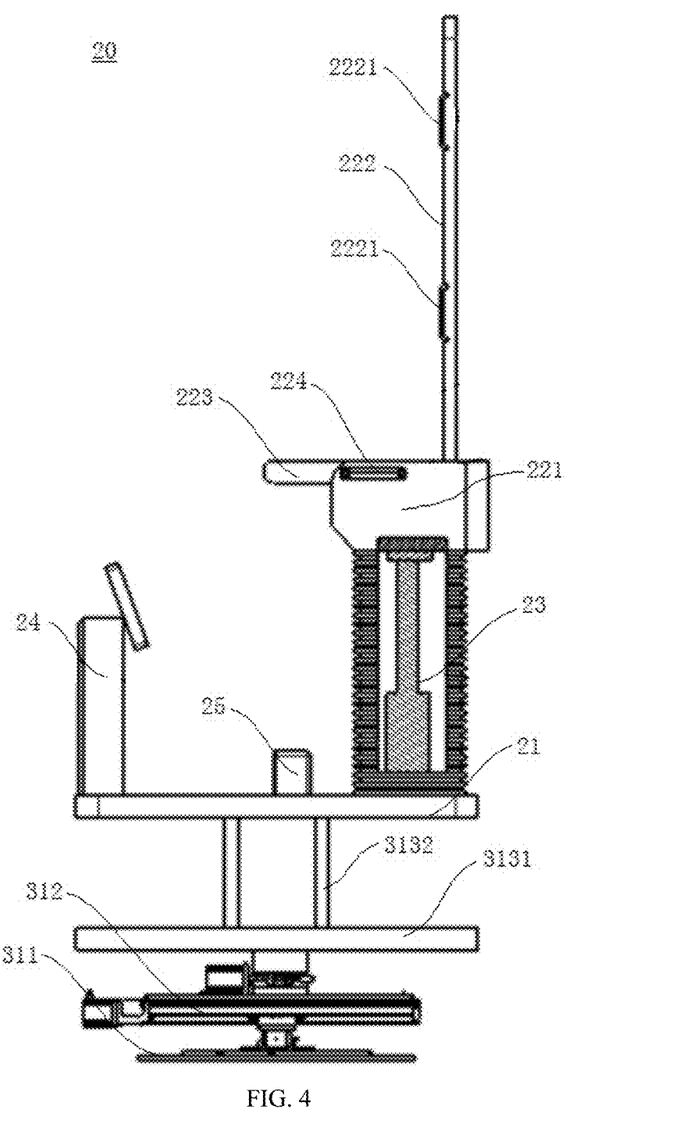
FIG. 4 schematically shows a structure of a treatment couch assembly according to an embodiment of the disclosure.

In an embodiment, the treatment couch assembly 20 includes a first base 21, a treatment couch main body 22 and a lifting-lowering assembly 23. The support and adjustment assembly 30 is connected to the first base 21 to drive the first base 21 to move, such that the position of the treatment couch assembly 20 with respect to the installation platform 10 can be adjusted.

Referring to FIG. 4, the treatment couch main body 22 is arranged on the first base 21, and is configured to fix the patient. The lifting-lowering assembly 23 is arranged above the first base 21, and is connected to the treatment couch main body 22 to drive the treatment couch main body 22 to move up or down, such that a position of the treatment couch main body 22 with respect to the first base 21 is adjusted, facilitating the treatment couch main body 22 to be matched with different patients.

It should be understood that the patients generally have different heights. When a patient is tall, the lifting-lowering assembly 23 drives the treatment couch main body 22 to move up to adjust the position of the treatment couch main body 22 with respect to the patient, so as to allow the treatment couch main body 22 to be matched with the patient. Similarly, when a patient is short, the lifting-lowering assembly 23 drives the treatment couch main body 22 to move down to adjust the position of the treatment couch main body 22 with respect to the patient, so as to allow the treatment couch main body 22 to be matched with the patient. A height of the treatment couch main body 22 can be adjusted according to a to-be-treated part of the patient, also, the adjustment method is simple and reliable.

In an embodiment, the treatment couch main body 22 includes a mounting base 221, a couch plate 222 and a cushion 223. The mounting base 221 is connected to the lifting-lowering assembly 23. The lifting-lowering assembly 23 is configured to drive the mounting base 21 to move, so as to adjust a height of the treatment couch main body 22 with respect to the first base 21.

Referring to FIG. 4, the couch plate 222 is arranged on the mounting base 221, and extends upwards along the vertical direction. The couch plate 222 is configured to deflect in a first direction to adjust depression and elevation angles of the couch plate 222. The first direction refers to a thickness direction of the couch plate 222. When the couch plate 222 needs to deflect an angle, the couch plate 222 can be deflected forward or backward around a joint part between the couch plate 222 and the mounting base 221.

In an embodiment, the cushion 223 is arranged on the mounting base 221, and at a bottom end of the couch plate 222. The cushion 223 is configured to be turned over. During use, the cushion 223 can be opened for sitting, and the patient can lean on the couch plate 222 to allow the back of the patient to fit the couch plate 222, such that the patient has a fixed sitting posture. When the cushion 223 is not in use, the cushion 223 can be folded to a vertical state to fit the couch plate 222, so as to reduce the space occupation.

The treatment couch assembly 20 can fix the patient with different postures, such as standing, half squatting and sitting, so as to adapt to treatments of multiple parts of the patient.

In an embodiment, the treatment couch main body 22 further includes multiple armrests 224. The armrests 224 are respectively arranged at two sides of the mounting base 221. The patient can keep the posture according to requirements by means of the armrests 224.

In an embodiment, the treatment couch main body 22 further includes multiple frames 2221. The frames 2221 are respectively arranged at two sides of the couch plate 222 to facilitate to keep the patient's posture.

It should be noted that during a preparation stage of treatment, the height of the treatment couch main body 22 is adjusted according to the to-be-treated part. An angle of the cushion 223 and that of the couch plate 222 are determined according to a required posture. When the patient sits on the cushion 223, the patient can keep the posture by means of the armrests 224 arranged at two sides of the mounting base 221. Meanwhile, the posture can be fixed through a combination of frames 2221 arranged at two sides of the couch plate 222 and a fixing net. The treatment couch assembly 20 is easy to be adjusted and reliable, and facilitates patient to keep the required posture according to different to-be-treated parts.

Referring to FIG. 4, in an embodiment, the treatment couch assembly 20 further includes a leg limit block 24 and feet limit block 25. The leg limit block 24 is arranged on the first base 21, and extends along the vertical direction from an upper surface of the first base 21. The leg limit block 24 is configured to limit legs of the patient. The foot limit block is arranged at the upper surface of the first base 21, and is located between the leg limit block 24 and the lifting-lowering assembly 23. The foot limit block 25 is configured to limit foot of the patient.

When the patient is required to fit the treatment couch main body, the patient can sit on the cushion 223. Legs of the patient abut against the leg limit block 24, such that the leg limit block 24 supports the legs of the patient. Feet of the patient locate between the leg limit block 24 and the foot limit block 25, such that the foot limit block 25 limits the feet of the patient. Consequently, the patient can keep the required posture.

In an embodiment, the lifting-lowering assembly 23 includes a telescopic electric cylinder and a telescopic sleeve. The telescopic electric cylinder is connected to a bottom of the mounting base 221. The telescopic sleeve is sleevedly arranged on an outside of the telescopic electric cylinder to shelter the telescopic electric cylinder, thereby preventing legs and foot of the patient from touching the telescopic electric cylinder, and preventing the telescopic electric cylinder from dust. The telescopic electric cylinder can be replaced by other equipment such as hydraulic cylinder.

In an embodiment, the support and adjustment assembly 30 includes a treatment couch adjustment assembly 31. The treatment couch adjustment assembly 31 is connected to the first base 21 of the treatment couch assembly 20, and is configured to adjust a position of the treatment couch assembly 20 with respect to the installation platform 10.

In an embodiment, the treatment couch adjustment assembly 31 includes a horizontal moving platform 311, a rotating platform 312 and a tilting platform 313. The horizontal moving platform 311 is configured to adjust a position of the first base 21 with respect to the installation platform 10 in the horizontal direction. The rotating platform 312 is connected to the horizontal moving platform 311. The rotating platform 312 is configured to drive the first base 21 to rotate horizontally with respect to the installation platform 10. The tilting platform 313 is connected between the rotating platform 312 and the horizontal moving platform 311. The tilting platform 313 is configured to drive the first base to tilt with respect to the installation platform 10. The horizontal moving platform 311, the rotating platform 312 and the tilting platform 313 are sequentially arranged from bottom to top. In consequence, through a movement coordination between the horizontal moving platform 311, the rotating platform 312 and the tilting platform 313, a tilt angle, a rotating angel and a horizontal position of the first base 21 with respect to the installation platform 10 can be adjusted.

In an embodiment, the support and adjustment assembly 30 is provided with a second base 33. The horizontal moving platform 311 is arranged on the second base 33. The horizontal moving platform 311 is connected to the treatment couch assembly 20 through the rotating platform 312 and the tilting platform 313. When the horizontal moving platform 311 moves with respect to the second base 33 to adjust a horizontal position of the horizontal moving platform 311 with respect to the installation platform 10, the rotating platform 312 and the tilting platform 313 synchronously move with the horizontal moving platform 311 to drive the treatment couch assembly 20 to move horizontally, such that the position of the treatment couch assembly 20 in the horizontal direction can be adjusted with respect to the installation platform 10.

In an embodiment, the rotating platform 312 is connected to the treatment couch assembly 20 through the tilting platform 313. When the rotating platform 312 rotates, the tilting platform 313 drives the treatment couch assembly 20 to rotate synchronously. The rotating platform 312 is configured to adjust an orientation of the treatment couch assembly 20 on the installation platform 10, that is, adjust a facing direction of the patient. It can be understood that by means of the rotating platform 312, the facing direction of the patient at the treatment couch assembly includes any horizontal direction, such as facing to left, right, front and back. The rotating platform 312 is configured to rotate around a vertical axis to adjust the orientation of the treatment couch assembly 20 in the horizontal direction.

Referring to FIG. 4, the tilting platform 313 is connected to the first base 21 of the treatment couch assembly 20 to adjust the tilt angle of the first base 21 with respect to the installation platform 10, so as to adjust depression and elevation angles of the treatment couch assembly 20. For example, the patient fixed to the treatment couch assembly 20 can be leans forward or backward.

It should be noted that the horizontal moving platform 311, the rotating platform 312 and the tilting platform 313 are sequentially arranged from bottom to top, which improves an adjustment stability of the treatment couch adjustment assembly 31. An adjustment method of the treatment couch adjustment assembly 31 is to stepwise adjust from bottom to top. A horizontal position of the treatment couch assembly 20 is adjusted through a horizontal movement of the horizontal moving platform 311, then the orientation of the treatment couch assembly 20 is adjusted through the rotating platform 312, finally, the depression and elevation angles of the treatment couch assembly 20 are adjusted through the tilting platform 313. The adjustment method is comprehensive and reliable.

In an embodiment, the tilting platform 313 includes a tilting platform main body 3131, a connecting rod assembly 3132 and a drive motor. The tilting platform main body 3131 is arranged above the rotating platform 312. The connecting rod assembly 3132 is connected between the tilting platform main body 3131 and the first base 21. When the connecting rod assembly 3132 swings with respect to the rotating platform 312, an incline angle of the first base 21 with respect to the tilting platform main body 3131 is adjusted.

The drive motor is connected to the connecting rod assembly 3132. The drive motor is configured to drive the connecting rod assembly 3132 to swing to tilt the first base 21 with respect to the tilting platform main body 3131, so as to adjust the depression and elevation angles of the treatment couch assembly 20. The connecting rod assembly 3132 includes a plurality of connecting rods. The connecting rods are configured to support the first base 21. The drive motor drives the connecting rods to swing to a certain angle, then the connecting rods are locked, such that the incline angle of the first base 21 is adjusted. The adjustment method is simple and reliable. It should be noted that the structure of the connecting rod assembly is designed as requirements, which is not limited here.

Figure 2:
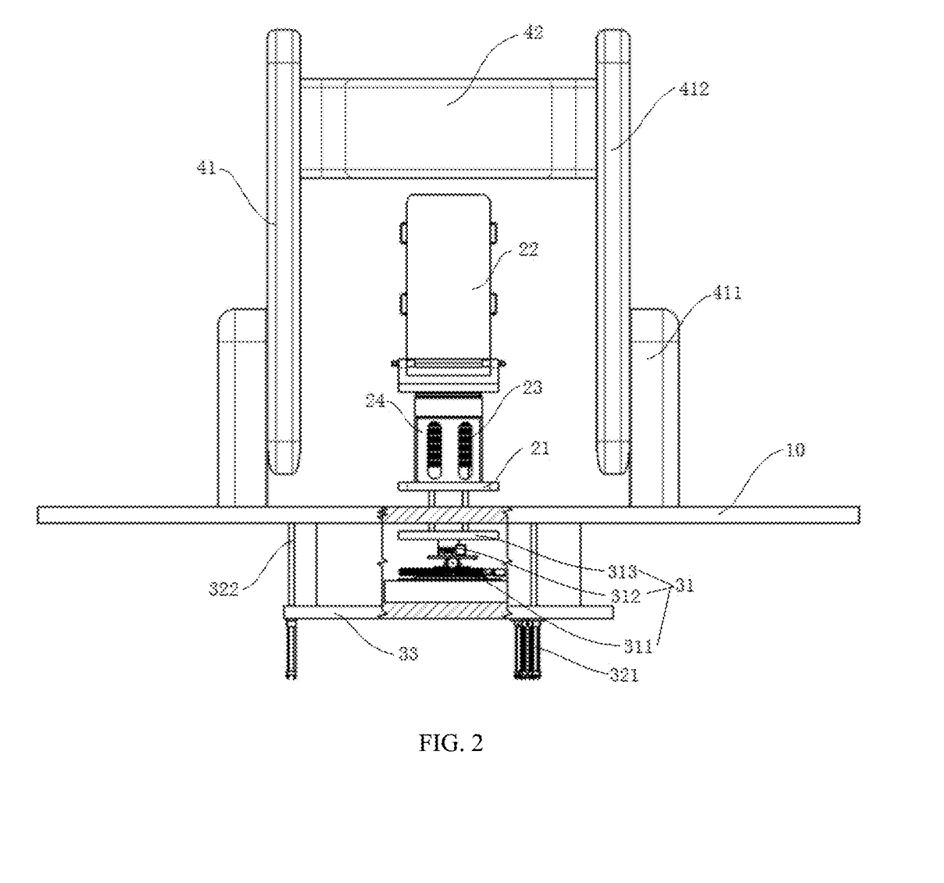
FIG. 2 is a front view of the patient sitting equipment according to an embodiment of the disclosure.

Referring to FIGS. 1-2, in an embodiment, the support and adjustment assembly 30 further includes a support assembly 32. The support assembly 32 is arranged at a bottom of the installation platform 10. The treatment couch assembly 20 is arranged on the support assembly 32. The support assembly 32 is configured to drive the installation platform 10 to move up or down, such that the height of the treatment couch assembly 20 with respect to the installation platform 10 is adjusted.

In an embodiment, the support and adjustment assembly 30 further includes a second base 33. The treatment couch adjustment assembly 31 is arranged on the second base 33. The support assembly 32 is connected between the second base 33 and the installation platform 10. The support assembly 32 includes an actuation cylinder 321 and a telescopic rod 322. The telescopic rod 322 is connected to the actuation cylinder 321. The actuation cylinder 321 is configured to drive the telescopic rod 322 to extend or retract. One end the telescopic rod 322 is connected to the actuation cylinder 321, and the other end of the telescopic rod 322 is connected to the installation platform 10. The actuation cylinder 321 is fixed on the second base 33. When the actuation cylinder 321 drives the telescopic rod 322 to retract, the support assembly 32 drives the second base 33 to move close to the installation platform 10, thereby driving the treatment couch adjustment assembly 31 to move upwards with respect to the installation platform 10. When the actuation cylinder 321 drives the telescopic rod 322 to extend, the support assembly 32 drives the second base 33 to move away from the installation platform 10, thereby driving the treatment couch adjustment assembly 31 to move downwards with respect to the installation platform 10.

Figure 5:
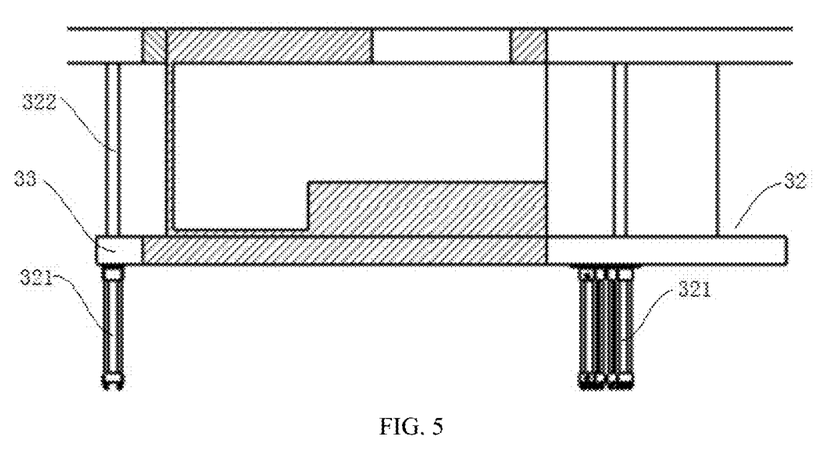
FIG. 5 schematically shows a structure of a support assembly according to an embodiment of the disclosure.

In an embodiment, multiple telescopic rods 322 and actuation cylinders 321 are provided, and the telescopic rods 322 are in one-to-one correspondence to the actuation cylinders 321. The telescopic rods 322 and actuation cylinders 321 are arranged evenly spaced apart along a circumferential direction of the second base 33, improving the stability of the support and adjustment assembly 30 when driving the second base 33 to move up or down with respect to the installation platform 10.

Figure 3:
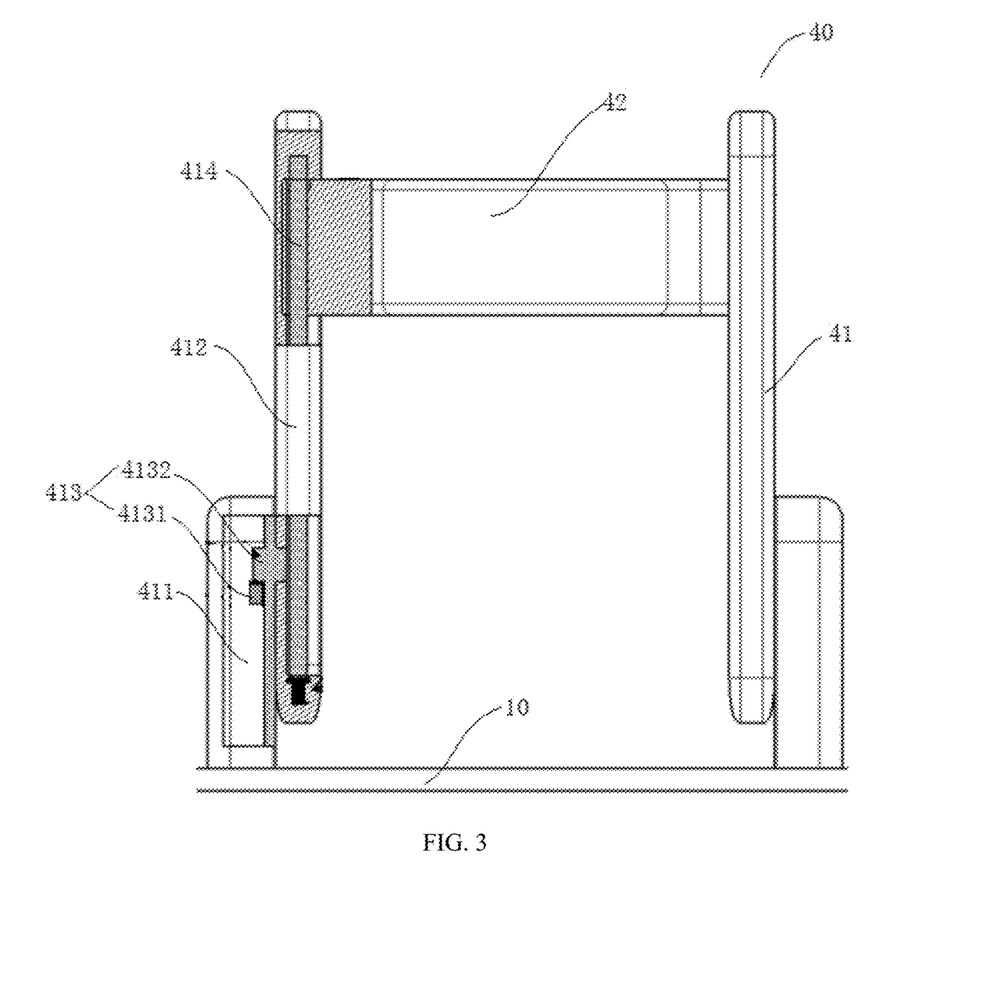
FIG. 3 schematically shows a structure of a 3D imaging assembly according to an embodiment of the disclosure.

Referring to FIG. 3, in an embodiment, the column assembly 41 includes a fixed column 411, a rotating column 412 and a rotating assembly 413. The fixed column 411 is arranged on the installation platform 10, and extends along the vertical direction. The 3D imaging device 42 is connected to the rotating column 412. The rotating column 412 is arranged at a side of the fixed column 411 close to the treatment couch assembly 20. The rotating column 412 is rotatably connected to the fixed column 411. The rotating assembly 413 is connected to the fixed column 411 and the rotating column 412. The rotating assembly 413 is configured to drive the rotating column 412 to rotate with respect to the fixed column 411.

Referring to FIG. 3, an incline angle of the rotating column 412 with respect to the installation platform 10 is adjusted through the rotating assembly 413, such that the scanning angle of the 3D imaging device is adjusted. The rotating assembly 413 includes a drive device 4131 and a slewing bearing 4132. The slewing bearing 4132 is connected between the rotating column 412 and the fixed column 411. The drive device 4131 is configured to drive the rotating column 412 to rotate with respect to the fixed column 411.

In an embodiment, the fixed column 412 is provided with a sliding groove 4121. The sliding groove 4121 extends along a length direction of the rotating column 412. The column assembly 41 further includes a drive member 414. The drive member 414 is connected to the rotating column 412 and the 3D imaging device 42. The drive member 414 is configured to drive the 3D imaging device 42 to slide with respect to the rotating column 412, so as to adjust a distance between the 3D imaging device 42 and the treatment couch assembly 20. Therefore, a distance between the 3D imaging device 42 and the patient can be adjusted, ensuring the scanning effect.

In an embodiment, the drive member 414 further includes a lead screw and a thread structure. The lead screw extends along the length direction of the rotating column 412, that is, the lead screw has the same extension direction to the sliding groove 4121. The thread structure is formed on the 3D imaging device 42. When the lead screw rotates, the 3D imaging device 42 is driven to slide along the rotating column 412.

Referring to FIG. 3, in an embodiment, the number of the column assemblies 41 is two. Two column assemblies 41 are respectively arranged at two sides of the treatment couch assembly 20. The 3D imaging device 42 is respectively connected to two rotating columns 412 of the two column assemblies 41. The two column assemblies 41 greatly support the 3D imaging device 42, improving the stability of the 3D imaging device 42 during adjustment.

Referring to FIGS. 1-5, an operation method of the patient sitting equipment 100 includes the following steps.

The installation platform is adjusted to a desired height.

A patient is fixed on the treatment couch assembly 20. For example, the patient sits on the cushion 223 and leans on the couch plate 222. The patient puts hands on the armrests 224. Feet of the patient are supported by the foot limit block 25. Legs of the patient are supported by the leg limit block 24. Then, a position of the treatment couch main body 22 with respect to the first base 21 is adjusted according to a figure of the patient, such that the treatment couch assembly 20 can match the patient's figure.

In an embodiment, when the patient need to deflect forward or backward, the frames 2221 and the fixing net are used to fix an upper body of the patient to the couch plate 222, so as to maintain the patient's posture.

In an embodiment, according to the to-be-treated part, the horizontal position, orientation and depression and elevation angles of the horizontal moving platform 311, the rotating platform 312 and the tilting platform 313 with respect to the treatment couch assembly 20 are adjusted.

Once the patient has been fixed with respect to the installation platform 10, a position of the 3D imaging device 42 with respect to the patient is adjusted through the drive member 414, including a distance between the 3D imaging device 42 and the patient and a scanning direction of the 3D imaging device 42 with respect to the patient. Consequently, the 3D imaging device 42 is at a position suited for image scanning.

It should be noted that the patient sitting equipment includes a scanning mode and a radiotherapy mode. Those components are adjusted in the same way in the scanning mode and in the radiotherapy mode.

In the scanning mode, the 3D imaging device 42 can scan the patient by moving along an extension direction of the rotating column 412. When the scanning is completed, the 3D imaging device 42 moves to a top of the rotating column 412. In the radiotherapy mode, a position and patient's posture are adjusted through the support and adjustment assembly 30 and the treatment couch assembly 20, thereby satisfying different radiotherapy requirements.

As used herein, terms "center", "vertical", "horizontal", "length", "width", "thickness", "top", "bottom", "front", "back", "left", "right", "vertical", "horizontal", "top", "bottom", "inside", "outside", "clockwise", "anticlockwise", "axial", "radial" and "circumferential" refer to orientational or positional relationship shown in the drawings, which are merely for better description of the present disclosure instead of indicating or implying that the device or element referred to must have a specific orientation, be constructed and operated in a specific orientation. Therefore, these terms should not be construed as a limitation to the present disclosure.

As used herein, the term "a plurality of" means two or more.

Terms "an embodiment", "some embodiments", "example", "specific example" and "some examples" means that the specific features, structures, materials, or characteristics described in conjunction with the embodiment or example are included in at least one embodiment or example of the present application. The above terms do not have to be directed to the same embodiment or example. Moreover, the specific features, structures, materials, or characteristics described may be combined in a suitable manner in any one or more embodiments or examples.

Described above are merely illustrative of the disclosure, and are not intended to limit the disclosure. Although the disclosure has been illustrated and described in detail above, it should be understood that those skilled in the art could still make modifications and changes to the embodiments of the disclosure. Those modifications, changes, replacements and variations made by those skilled in the art based on the content disclosed herein without departing from the scope of the disclosure shall fall within the scope of the present disclosure defined by the appended claims.

What is claimed is:

1. Patient sitting equipment for radiotherapy, comprising:
an installation platform;
a treatment couch assembly;
a support and adjustment assembly; and
a three-dimensional (3D) imaging assembly;
wherein the treatment couch assembly is configured to fix a patient, and the treatment couch assembly comprises a base, a treatment couch main body, a lifting-lowering assembly, a leg limit block and a feet limit block;
wherein the base is connected to the support and adjustment assembly;
the treatment couch main body is arranged on the base and is configured to fix the patient; and the treatment couch main body comprises a mounting base, a couch plate and a cushion;
wherein the mounting base is connected to the lifting-lowering assembly; the couch plate is arranged on the mounting base, and extends upwards along the vertical direction; the couch plate is configured to deflect in a first direction with respect to the mounting base to adjust depression and elevation angles of the couch plate; the cushion is arranged on the mounting base, and at a bottom end of the couch plate; and the cushion is configured to be turned over;
the lifting-lowering assembly is arranged above the base, and is connected to the treatment couch main body to drive the treatment couch main body to move up or down;
the leg limit block is arranged on the base, and extends along the vertical direction from an upper surface of the base; and the leg limit block is configured to limit legs of the patient;
the feet limit block is arranged at the upper surface of the base, and is located between the leg limit block and the lifting-lowering assembly; and the feet limit block is configured to limit feet of the patient;
the support and adjustment assembly is arranged below the installation platform; the support and adjustment assembly is connected to the treatment couch assembly, and is configured to adjust a position of the treatment couch assembly with respect to the installation platform; the support and adjustment assembly comprises a treatment couch adjustment assembly; and the treatment couch adjustment assembly is connected to the base of the treatment couch assembly;
the treatment couch adjustment assembly comprises a horizontal moving platform, a rotating platform and a tilting platform;
the horizontal moving platform is configured to adjust a position of the base with respect to the installation platform in the horizontal direction; the rotating platform is connected to the horizontal moving platform; the rotating platform is configured to drive the base to rotate horizontally with respect to the installation platform; the tilting platform is connected between the rotating platform and the base; the tilting platform is configured to drive the base to tilt with respect to the installation platform; and the horizontal moving platform, the rotating platform and the tilting platform are sequentially arranged from bottom to top;
the tilting platform comprises a tilting platform main body, a connecting rod assembly and a drive motor; the tilting platform main body is arranged above the rotating platform; the connecting rod assembly is connected between the tilting platform main body and the base; the drive motor is connected to the connecting rod assembly; and the drive motor is configured to drive the connecting rod assembly to move to tilt the base with respect to the tilting platform main body; and
the 3D imaging assembly comprises a column assembly and a 3D imaging device; the column assembly is arranged at the installation platform, and extends along the vertical direction; the 3D imaging device is movably arranged at the column assembly; the 3D imaging device is corresponding to the treatment couch assembly in a horizontal projection direction; and the 3D imaging device is configured to perform image scanning on the patient.

2. The patient sitting equipment of claim 1, wherein the column assembly comprises a fixed column, a rotating column and a rotating assembly;
the fixed column is arranged on the installation platform, and extends along the vertical direction;

the 3D imaging device is connected to the rotating column; the rotating column is arranged at a side of the fixed column close to the treatment couch assembly; and the rotating column is rotatably connected to the fixed column; and the rotating assembly is connected to the fixed column and the rotating column; and the rotating assembly is configured to drive the rotating column to rotate with respect to the fixed column.

3. The patient sitting equipment of claim 2, wherein the rotating column is provided with a sliding groove; the sliding groove extends along a length direction of the rotating column; and the column assembly further comprises a drive member; the drive member is connected to the rotating column and the 3D imaging device; and the drive member is configured to drive the 3D imaging device to slide with respect to the rotating column.

4. The patient sitting equipment of claim 2, wherein the number of the column assembly is two; two column assemblies are respectively arranged at two sides of the treatment couch assembly; and the 3D imaging device is respectively connected to two rotating columns of the two column assemblies.

5. The patient sitting equipment of claim 1, wherein the support and adjustment assembly further comprises a support assembly; the support assembly is arranged at a bottom of the installation platform; the treatment couch adjustment assembly is arranged on the support assembly; and the support assembly is configured to drive the treatment couch adjustment assembly to move up or down with respect to the installation platform.

\* \* \* \* \*